United States Patent
Hareland

(10) Patent No.: US 12,004,794 B2
(45) Date of Patent: Jun. 11, 2024

(54) ACTIVE PRESSURE CONTROL AND METHOD OF FAULT MONITORING

(71) Applicant: Medtronic CryoCath LP, Toronto (CA)

(72) Inventor: Scott A. Hareland, Lino Lakes, MN (US)

(73) Assignee: Medtronic CryoCath LP, Toronto (CA)

( * ) Notice: Subject to any disclaimer, the term of this patent is extended or adjusted under 35 U.S.C. 154(b) by 960 days.

(21) Appl. No.: 16/706,019

(22) Filed: Dec. 6, 2019

(65) Prior Publication Data
US 2021/0169545 A1 Jun. 10, 2021

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00577* (2013.01); *A61B 2018/00791* (2013.01); *A61B 2018/00863* (2013.01); *A61B 2018/0212* (2013.01); *A61B 2562/0247* (2013.01)

(58) Field of Classification Search
CPC .......................... A61B 18/02; A61M 25/10184
See application file for complete search history.

(56) References Cited

U.S. PATENT DOCUMENTS

| | | | |
|---|---|---|---|
| 4,924,862 A | | 5/1990 | Levinson |
| 5,501,681 A | * | 3/1996 | Neuwirth ............... A61B 18/08 |
| | | | 607/104 |
| 5,599,301 A | | 2/1997 | Jacobs et al. |
| 2005/0038421 A1 | * | 2/2005 | Joye ....................... A61B 18/02 |
| | | | 606/20 |

(Continued)

FOREIGN PATENT DOCUMENTS

| | | |
|---|---|---|
| WO | 2006006990 A2 | 1/2006 |
| WO | 2011142758 A1 | 11/2011 |

(Continued)

OTHER PUBLICATIONS

International Search Report and Written Opinion dated Dec. 2, 2020, for corresponding International Application No. PCT/CA2020/051270; International Filing Date: Sep. 23, 2020 consisting of 14 pages.

(Continued)

*Primary Examiner* — Ronald Hupczey, Jr.
(74) *Attorney, Agent, or Firm* — Michael Best & Friedrich LLP

(57) ABSTRACT

A medical system for monitoring pressure may comprise a medical device with an expandable element, at least one pressure sensor in communication with the expandable element and a control unit. The control unit may include a fluid source in fluid communication with the expandable element and circulation of the fluid within the expandable element may inflate the expandable element. A processing circuitry may be configured to monitor a pressure within the (Continued)

expandable element based on signals received from the at least one pressure sensor for a first period of time and circulation of the fluid within the expandable element for a second period of time.

18 Claims, 3 Drawing Sheets

(56) References Cited

U.S. PATENT DOCUMENTS

| | | | |
|---|---|---|---|
| 2006/0129142 A1* | 6/2006 | Reynolds | A61B 18/02 607/113 |
| 2008/0114428 A1* | 5/2008 | Trembly | A61B 18/20 607/100 |
| 2008/0119785 A1 | 5/2008 | Ramsey et al. | |
| 2009/0299356 A1 | 12/2009 | Watson | |
| 2012/0029495 A1 | 2/2012 | Wittenberger | |
| 2013/0023920 A1 | 1/2013 | Terliuc et al. | |
| 2015/0250524 A1 | 9/2015 | Moriarty et al. | |
| 2018/0036166 A1 | 2/2018 | Burnett et al. | |

FOREIGN PATENT DOCUMENTS

| | | |
|---|---|---|
| WO | 2014189601 A1 | 11/2014 |
| WO | 2018182913 A1 | 10/2018 |

OTHER PUBLICATIONS

European Patent Office Extended Search Report for Application No. 20895803.3 dated Feb. 26, 2024 (14 pages).

* cited by examiner

ACTIVE PRESSURE CONTROL AND METHOD OF FAULT MONITORING

CROSS-REFERENCE TO RELATED APPLICATION n/a.

FIELD

The present technology is generally related to a cryoablation device having an expandable treatment element, as well as methods and systems for active pressure control and leakage monitoring and detection of the expandable treatment element.

BACKGROUND

Cardiac arrhythmias and other cardiac conditions are widely treated with catheters that have an expandable treatment element. These types of catheter based devices may be desirable in a variety of different medical and surgical applications and settings as the use of this type of medical device is not particularly invasive and may allow for targeted treatment of localized tissue. Catheters with expandable treatment elements may be inserted into the body and navigated through blood vessels to a target site with minimal trauma to the body.

Inflation and deflation of the expandable treatment element may be necessary for the placement of the catheter within the body as well as for the delivery of localized therapy to areas of the body that are difficult to access. For example, ablation and cryoablation treatment may be delivered to certain tissue using an expandable treatment catheter where, for example, the expandable treatment element is filled and pressurized with a gas or fluid and can be movable through vessels to different parts of the body. Effective contact with tissue may require movement, positioning, anchoring, stabilizing, and changing the shape of the expandable treatment element to conform to the particular area of tissue being treated. Slight changes in orientation and pressure of the expandable treatment element may greatly impact how well treatment is delivered to a particular area of tissue. The effectiveness and efficiency of an ablation and/or cryoablation procedure may depend upon the pressure that is maintained within the expandable treatment element during a procedure and well as how and where the expandable treatment element is placed within the body.

Additionally, the operation of a catheter that has an expandable treatment element may require that fluid or gas that is injected into the expandable treatment element be contained within the catheter at all times. A leak in the expandable treatment element and/or any portion of the catheter could cause significant harm to the patient that is receiving treatment. For example, if a unitary expandable treatment element develops a crack, leak, rupture, or other structural integrity failure, a fluid or gas may flow out of the catheter and into the body.

SUMMARY

The techniques of this disclosure generally relate to the cryoablation of tissue with a cryoablation device having an expandable treatment element, as well as systems and methods for active pressure control and leakage monitoring and detection of the expandable treatment element. In one embodiment, the medical system for monitoring pressure comprises: a medical device, including: an expandable element; at least one pressure sensor in communication with the expandable element; and a control unit including: a fluid source in fluid communication with the expandable element, circulation of the fluid within the expandable element inflates the expandable element; and a processing circuitry configured to monitor a pressure within the expandable element based on signals received from the at least one pressure sensor for a first period of time and circulation of the fluid within the expandable element for a second period of time.

In one aspect of the embodiment, the processing circuitry alternates between monitoring the pressure within the expandable element for the first period of time and circulating the fluid within the expandable element for the second period of time for a predetermined period of time.

In one aspect of the embodiment, the predetermined period of time is the duration of a medical procedure.

In one aspect of the embodiment, the first period of time and the second period of time are the same period of time.

In one aspect of the embodiment, the first period of time is longer than the second period of time.

In one aspect of the embodiment, the first period of time is shorter than the second period of time.

In one aspect of the embodiment, the circulation of the fluid within the expandable element stops when the processing circuitry is monitoring the pressure within the expandable element based on signals received from the at least one pressure sensor.

In one aspect of the embodiment, the expandable element is inflated to a preset pressure with the circulation of the fluid within the expandable element and then the processing circuitry stops the circulation of the fluid within the expandable element for a third period of time.

In one aspect of the embodiment, the processing circuitry is set to a predetermined pressure threshold and when the pressure in the expandable element exceeds the predetermined pressure threshold, the processing circuitry signals a fault condition.

In one aspect of the embodiment, when the pressure in the expandable element falls below the predetermined pressure threshold, the processing circuitry signals a fault condition.

In one aspect of the embodiment, the fault condition discontinues fluid circulation in the expandable element.

In one embodiment, a medical system for monitoring pressure comprises: a medical device, including: an expandable element; and a control unit including: a fluid source in fluid communication with the expandable element, circulation of the fluid within the expandable element inflating the expandable element to a preset pressure range, once a pressure of the expandable element is within the preset pressure range, the fluid source provides preset periodic inflation pulses to the expandable element; and a processing circuitry configured to monitor at least one of a duration and a frequency of the preset periodic inflation pulses to determine any changes to at least one of the frequency and the duration of the preset periodic inflation pulses.

In one aspect of the embodiment, the expandable element is a balloon.

In one aspect of the embodiment, the preset pressure range is adjustable.

In one aspect of the embodiment, the frequency and the duration of the periodic inflation pluses is adjustable.

In one aspect of the embodiment, a change in at least one of the frequency and the duration of the preset periodic inflation pulses signals a fault condition.

In one aspect of the embodiment, the fault condition provides at least one of a notification and activation of a system response.

In one aspect of the embodiment, the system response is an evacuation of fluid from the medical device.

In one aspect of the embodiment, the fluid source is a cryogenic fluid.

In one embodiment, a medical system for monitoring pressure comprises: a medical device, including: an expandable element; at least one pressure sensor in communication with the expandable element; and a control unit configured to operate in a first mode and a second mode: in the first mode, a fluid circulates through the expandable element causing the expandable element to inflate for a first period of time and a processing monitors a pressure within the expandable element based on signals received from the at least one pressure sensor for a second period of time; and in the second mode, the fluid circulates within the expandable element and inflates the expandable element to a preset pressure range, then a fluid source provides preset periodic inflation pulses to the expandable element, a processing circuitry is configured to monitor the preset periodic inflation pulses to the expandable element and determine any changes to at least one of a frequency and a duration of the preset period inflation pulses.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
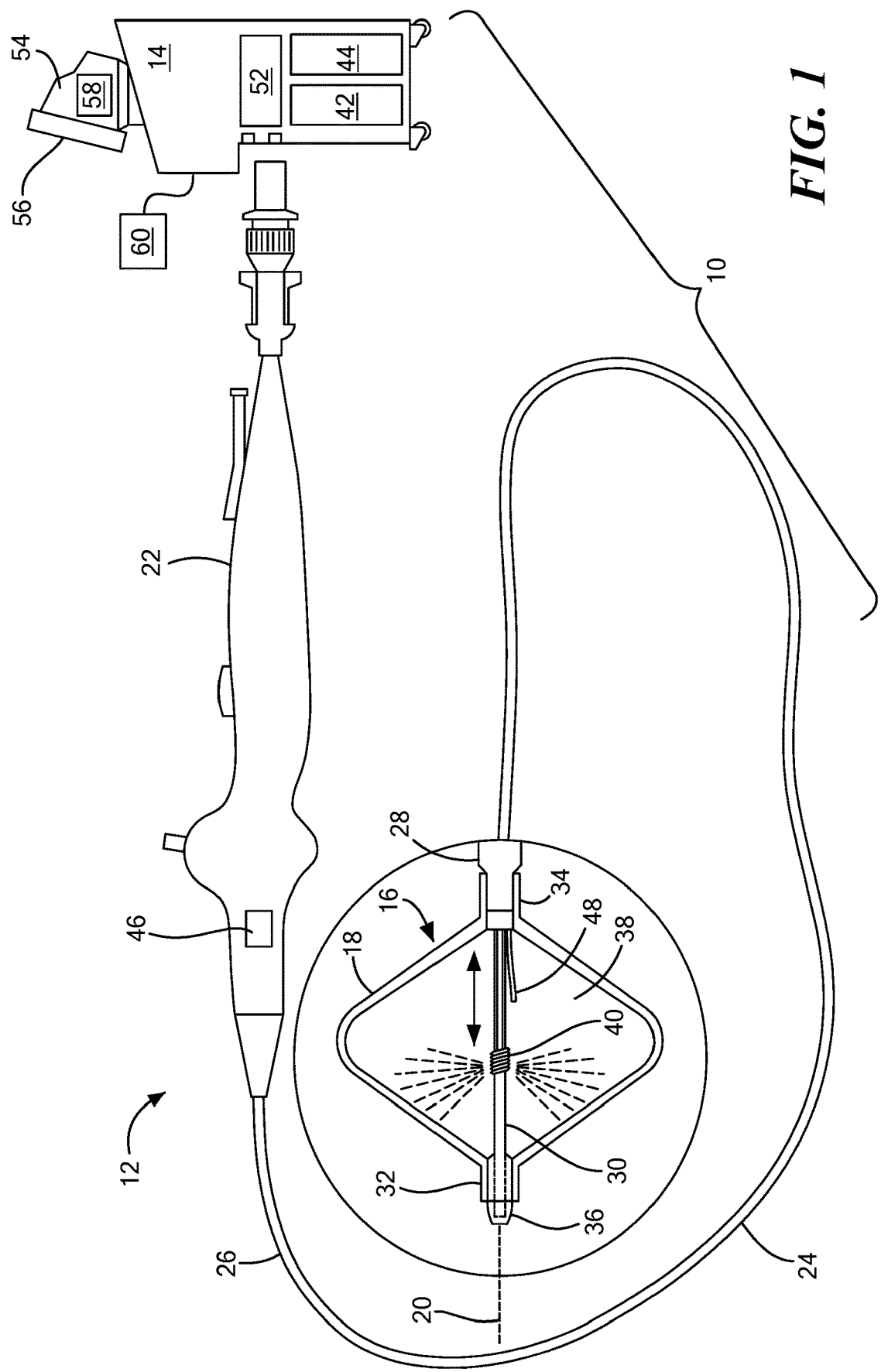
FIG. 1 shows an exemplary medical system in accordance with the present disclosure, the medical system including a cryoablation device with an expandable element.

The devices, systems, and methods disclosed herein are for assessing the pressure in an expandable element and monitoring the leakage of any fluid and/or gas from the expandable element. In one embodiment, a medical system for assessing pressure in an expandable element and monitoring leakage includes an elongate body including a distal portion and a proximal portion and an expandable element coupled to the elongate body distal portion. The expandable element may have a first expandable element, a second expandable element, and the first expandable element may be within the second expandable element. The expandable element may have more than two expandable elements or may be one unitary expandable element.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible for achieving the electrical and data communication.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Referring now to the drawing figures in which like reference designations refer to like elements, an embodiment of a medical system is shown in FIG. 1, generally designated as "10." The device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

Continuing to refer to FIG. 1, an exemplary medical system 10 for cryoablation is shown. One embodiment of the medical system 10 may generally include a treatment device, such as a cryoablation treatment device 12, and a control unit 14 in communication with the cryoablation treatment device 12. The cryoablation treatment device 12 may include one or more diagnostic or treatment elements 16 for energetic or other therapeutic interaction between the cryoablation treatment device 12 and a treatment site. The treatment element(s) 16 may deliver, for example, cryogenic therapy, and may further be configured to deliver radiofrequency energy, or otherwise for energetic transfer with a tissue area in proximity to the treatment region(s), including cardiac tissue. In particular, the one or more treatment elements 16 may be configured to reduce the temperature of adjacent tissue in order to perform cryotreatment and/or cryoablation. Additionally, the cryoablation treatment device 12 may be used for treatment, denervation, or nerve modulation.

Continuing to refer to FIG. 1, the treatment element 16 may include one or more expandable elements and/or inflatable elements such as balloons (as shown in FIG. 1) within which a coolant is circulated in order to reduce the temperature of the balloon(s) 18 and, as a result, to reduce the temperature of tissue that is in contact with and/or adjacent to the balloon(s) 18. Where the application refers to the balloon 18 and/or the balloon(s), it will be understood that this may also be referring to expandable element(s) and/or inflatable element(s) and that the balloon 18 is only an exemplary embodiment. Additionally, in some embodiments, the balloon(s) 18 include other thermally and/or electrically-conductive elements, such as one or more electrodes (not shown) in communication with the control unit 14. Further, although one balloon 18 is shown in the figures, it will be understood that the cryoablation treatment device 12 may include more than one balloon 18 positioned next to each other and/or layered on top of each other. For example, the treatment element 16 may include a first balloon positioned within a second balloon (not shown).

Continuing to refer to FIG. 1, in one embodiment, in addition to the treatment element(s) 16, the cryoablation treatment device 12 also defines a longitudinal axis 20 and generally includes a handle 22 and an elongate body 24 coupled to the handle 22. The elongate body 24 may be sized and configured to be passable through a patient's vasculature and/or positionable proximate to a tissue region for diagnosis or treatment, such as a catheter, sheath, or intravascular introducer. The elongate body 24 may define a proximal portion 26 coupled to the handle 22, a distal portion 28 opposite the proximal portion 26, and may further include one or more lumens disposed within the elongate body 24 that provide mechanical, electrical, and/or fluid communication between the proximal portion 26 and the distal portion 28 of the elongate body 24.

In one embodiment, at least a portion of the treatment element(s) 16 is coupled to the distal portion 28 of the elongate body 24. In one embodiment, the cryoablation treatment device 12 further includes a shaft 30 that is longitudinally movable within the elongate body 24 (for example, within a central lumen of the elongate body 24) such that the shaft is advanceable and retractable within the elongate body 24. In one embodiment, the at least one treatment element 16 includes a balloon 18 having a distal neck 32 and a proximal neck 34, and the distal neck 32 is coupled to a distal tip 36 of the shaft 30 and the proximal neck 34 is coupled to the distal portion 28 of the elongate body 24. In this configuration, movement of the shaft 30 within the elongate body 24 affects the shape and/or configuration of the balloon 18. For example, the shaft 30 may be fully advanced when the balloon 18 is deflated and in a delivery (or first) configuration wherein the balloon 18 has a minimum diameter suitable, for example, for retraction of the cryoablation treatment device 12 within a sheath for delivery to and/or removal from a target treatment site. Conversely, when the balloon 18 is inflated or expanded and in a treatment (or second) configuration, the shaft 30 may be advanced or retracted over a distance that affects the size and/or configuration of the inflated or expanded balloon 18 (for example, as indicated by the double-headed arrow in FIG. 1). Further, the shaft 30 may include a guidewire lumen through which a sensing device, mapping device, guidewire, or other system component may be passed.

Continuing to refer to FIG. 1, in one embodiment the balloon 18 defines an interior chamber 38 and the cryoablation treatment device 12 further includes one or more nozzles, orifices, or other fluid delivery elements 40 for delivering fluid, such as coolant, to the interior chamber 38 of the balloon 18. During operation, in one embodiment, coolant flows from a coolant supply reservoir 42 through a fluid flow path that is located at least partially within the elongate body 24 of the cryoablation treatment device 12 to the balloon 18. Coolant then enters the interior chamber 38 of the balloon 18, such as through the fluid delivery element(s) 40, after which the coolant expands to cool the balloon 18. Expanded coolant then passes from the interior chamber 38 of the balloon 18 to a coolant recovery reservoir 44 and/or scavenging/exhaust system (not shown).

Continuing to refer to FIG. 1, one embodiment of the medical system 10 further includes a pressure sensing system 46 that includes a pressure sensor 48 (for example, a pressure transducer) within the handle and/or control unit 14 and/or a pitot tube 50 in fluid communication with the pressure sensor 48. In one embodiment, the pressure sensor 48 is located within the handle 22 and the pitot tube 50 extends from the pressure sensor 48 to a location within the interior chamber 38 of the balloon 18, and the pitot tube 50 includes one or more orifices (not shown) that are configured to be exposed to fluid and/or gas circulating within the interior chamber 38 when the cryoablation treatment device 12 is in use. According to known principles, the pitot tube 50 and pressure sensor 48 measure a dynamic pressure based on a difference between a stagnation pressure and a static pressure. Accordingly, in one embodiment, the sensing system 46 is configured to measure a pressure within the interior chamber 38, which correlates to the pressure of the balloon 18. In some embodiments, the cryoablation treatment device 12 and/or the control unit 14 includes one or more additional sensors, such as temperature sensors, flow rate sensors, pressure sensors, impedance sensors, or the like.

Continuing to refer to FIG. 1, in one embodiment the control unit 14 generally includes one or more reservoirs, including the coolant supply reservoir 42, the coolant recovery reservoir 44, and other components of the fluid flow path, such as a vacuum pump 52 for creating a low-pressure environment in one or more conduits of the fluid flow path so that expanded coolant is drawn from the interior chamber 38 of the balloon 18 and toward the proximal portion 26 of the elongate body 24 and into the coolant recovery reservoir 44. In some embodiments, the control unit 14 also includes an energy generator (not shown). As used herein, the term "control unit" refers to any components of the medical system 10 other than components of the cryoablation treatment device 12 itself, regardless of whether the components are physically located within or external to the control unit 14.

Continuing to refer to FIG. 1, in one embodiment the control unit 14 also includes one or more controllers, processors, and/or software modules containing instructions or algorithms to provide for the automated or semi-automated operation and performance of the features, sequences, or procedures described herein. In one embodiment, the control unit 14 includes a computer 54 having a display 56 and processing circuitry 58 programmed or programmable to execute the automated or semi-automated operation and performance of the features, sequences, calculations, and/or procedures described herein. In one embodiment, the processing circuitry 58 includes a memory and a processor, the memory including instructions that, when executed by the processor, configured the processor to receive, process, or otherwise use signals from the cryoablation treatment device 12 and/or other system components. Additionally, in some embodiments the control unit 14 further includes one or more user input devices 60 (such as a keyboard, touchscreen, keypad, button, knob, or the like), controllers, speakers, and/or displays that are in communication with processing circuitry 58 and used for collecting and conveying information from and to the user.

Continuing to refer to FIG. 1, the processing circuitry 58 may be in communication with the sensing system 46 and may be configured to monitor the pressure within the balloon 18 in real-time based upon signals received from the pressure sensor 48 and the pitot tube 50. Alternatively, the sensing system 46 may include pressure monitoring circuitry that includes a pressure sensor 48 that may be located within the control unit 14. The pressure in the balloon 18 may be measured by the pressure sensor 48 in the control unit 14. For example, the interior chamber 38 of the balloon 18 may be in communication with the pressure monitoring circuitry of the control unit 14 through, for example, an injection tube or a vacuum pathway between the balloon 18 and the control unit 14 and can therefore measure the pressure inside the balloon 18. In general, pressure control within the balloon 18 is desired so that the balloon 18 may be inflated or deflated over a range of different pressures which may be necessary to achieve certain clinical goals. When real-time pressure control is required for a particular medical procedure, the sensing system 46 may not detect leakage in the balloon 18 as the cryoablation treatment device 12 may be able to compensate for some leakage by, for example, increasing the circulation of fluid within the balloon 18. However, in some medical procedures, even a small pressure loss could impact the stiffness and rigidity of the balloon 18 such that it is not as easy to occlude at a particular pressure.

Figure 2:
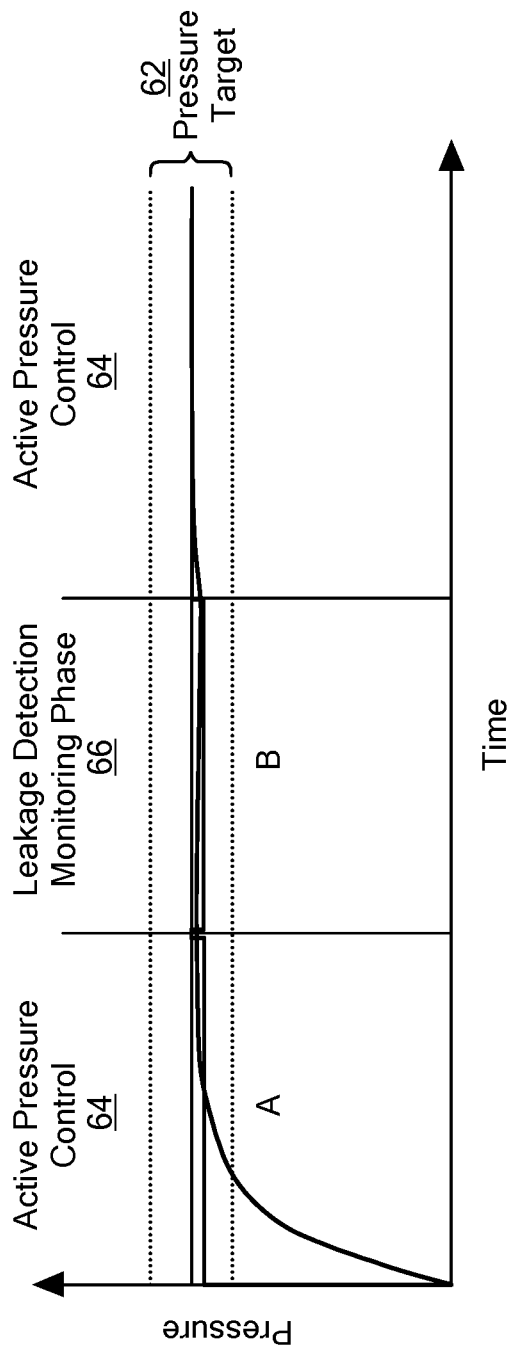
FIG. 2 shows a chart of exemplary data demonstrating the pressure of the expandable element and the processing circuitry alternating between an active pressure control and a leakage detection monitoring phase where the pressure is maintained within a predetermined threshold.

Now referring to FIG. 2, in one embodiment, the control unit 14 may be configured to alternative between an active pressure control 64 and a leakage detection monitoring phase 66. In the active pressure control 64, the balloon 18 may be inflated to a particular preset pressure target 62 wherein the coolant supply reservoir 42 is in fluid communication with the balloon 18 and the coolant may flow from the coolant supply reservoir 42 through the lumen to the balloon 18 and inflate the balloon 18 to a preset pressure target 62. The processing circuitry 58 may be configured to detect whether the balloon 18 has been inflated to the preset pressure target 62. It will be understood that although coolant is generally referred to, any fluid or gas may be used to inflate the balloon 18. The pressure target 62 may be one particular pressure or it may encompass a range of pressures throughout the course of a medical procedure. In one embodiment, the active pressure control 64 may be when the control unit 14 inflates the balloon 18 to the pressure target 62. For example, the pressure target 62 may be set to a range of different pressures so that the balloon 18 may be inflated and/or deflated to a variety of different pressures. For example, the balloon 18 may be inflated to a positive pressure with respect to the atmospheric pressure and as a non-liming example the balloon 18 may be inflated to a pressure between 20 psi and 120 psi. The pressure in the balloon 18 may be set to a variety of different pressures depending upon the type of balloon 18 being used, the procedure that is being performed, as well as the anatomy of the patient. The active pressure control 64 may maintain the balloon 18 at a preset pressure for a period of time where coolant is continually flowing from that coolant supply reservoir 42 into the balloon 18. Alternatively, the active pressure control 64 may maintain the balloon 18 at a preset pressure for the period of time by periodically injecting coolant from the coolant supply reservoir 42 to the balloon 18. Once the balloon 18 is inflated to the preset pressure target 62, the control unit 14 may stop the circulation of the fluid within the balloon 18 for a period of time. In the medical system 10, whenever fluid and/or gas is initially injected into the balloon 18, the pressure in the balloon 18 may temporarily increase based upon the initial cooling effect of the fluid and/or gas. However, once the fluid and/or gas inside the balloon 18 is warmed by the body including any tissue and/or blood around the balloon 18, the pressure inside the balloon 18 may decrease. The control unit 14 may be configured to recognize this temporary pressure change when a fluid and/or gas is initially injected into the balloon 18 causing the pressure inside the balloon 18 to temporarily increase and then once the gas/fluid is warmed by the body, the pressure inside the balloon 18 may decrease. When the control unit 14 recognizes this pressure change, it may be identified as a normal pressure fluctuation that does not trigger any alerts, system responses, and/or notifications. The amount of coolant or other gas or fluid flowing from the coolant supply reservoir 42 into the balloon 18 may be adjusted based upon how much coolant is required to maintain the pressure target 62 in the balloon 18. This may be customized to the particular medical procedure being performed as well as the needs and requirements of the patient that is having the medical procedure. The pressure target 62 may be the same pressure throughout an entire medical procedure or the control unit 14 may be configured to adjust the pressure target 62 throughout the course of the medical procedure at certain preset time intervals or based upon the anatomy that is being encountered by the medical device 10. Alternatively, an individual may be able to input the pressure target 62 into the control unit 14 manually, for example, by using the input device 60. This manual entry of the pressure target 62 may allow for adjustments when unexpected conditions are found during a medical procedure which require the pressure target 62 in the balloon 18 to be changed.

Continuing to refer to FIG. 2, the control unit 14 may also be configured to disable the active pressure control 64 where coolant is continually flowing from the coolant supply reservoir 42 into the balloon 18. When the active pressure control 64 is disabled, the control unit 14 may enter the leakage detection monitoring phase 66. In the leakage detection monitoring phase 66, the control unit 14 may actively monitor the pressure of the balloon 18 using the pressure sensor 48 and the pitot tube 50 in the sensing system 46 to determine any changes in pressure within the balloon 18 or the pressure may be monitored anywhere else in the cryoablation treatment device 12 when coolant is not flowing from the coolant supply reservoir 42 into the balloon 18. The control unit 14 may have certain preset parameters for the pressure target 62 to indicate whether any loss of pressure in the balloon 18 or anywhere else in the cryoablation treatment device 12 is within the preset pressure range. The medical system 10, including the cryoablation treatment device 12, may also include a safety pressure monitoring system to detect unwanted build-up of pressure outside the interior chamber 38 of the balloon 18 but inside the cryoablation treatment device 12. The preset parameters for the pressure target 62 may include measured changes in pressure from the initial pressure level, for example −0.5 psi from the initial pressure level, or it may be based upon a measured rate of pressure change over time, for example, a pressure change of less than 1 psi/min over a time scale of (t) seconds. There may also be levels of pressure changes that are set to respond based upon different time scales, for example, less than 1 psi/min for 10 second, or less than 2 psi/min for 2 seconds, or less than 5 psi/min for 0.2 seconds. Including pressure level changes that are set to respond at different time scales may allow for a faster response to larger pressure changes any may also provide the medical system 10 more time to evaluate smaller pressure changes to reduce the risk of reporting a leakage if no leakage exists. Also, certain changes in the pressure of the balloon 18 in the leakage detection monitoring phase 66 may be normal and expected while other pressure changes in the pressure of the balloon 18 may indicate that there is a leak in the balloon 18 or a leak elsewhere in the medical system 10. Pressure leaks in the medical system 10 may exist that are unrelated to the structural integrity of the balloon 18. For example, pressure leaks of less than an few 0.1 psi/min may be normal and expected within the medical system 10. The range of what is considered to be normal and expected pressure loss within any particular medical system 10 may be set based upon the parameters of the particular system and can vary based upon the requirements of the medical system 10 as well as the procedure being performed. If the pressure of the balloon 18 remains in the pressure target 62 range while in the leakage detection monitoring phase 66, the control unit 14 may return back to the active pressure control 64. Alternatively, if the pressure of the balloon 18 falls before the pressure target 62 range, than the control unit 14 may have the cryoablation treatment device 12 remain in the leakage detection monitoring phase 66 so that fluid and/or gas is not supplied to the balloon 18, and/or may discontinue the operation of the cryoablation treatment device 12 so that any fluid and/or gas that may be leaking from the balloon 18 is not released into the body of the patient.

In one embodiment as shown in FIG. 2, the control unit 14 may be configured to alternate between the active pressure control 64 and the leakage detection monitoring phase 66. In FIG. 2, the active pressure control 64 may be set for the same period of time as the leakage detection monitoring phase 66. For example, during the medical procedure, the control unit 14 may be configured to be in active pressure control 64 for a first period of time A, one (1) minute, and then alternate to the leakage detection monitoring phase 66 for a second period of time B, one (1) minute such that this alternating between the first period of time A and the second period of time B occurs for the duration of the medical procedure. Alternatively, the alternating between the first period of time A and the second period of time B may be for less than the duration of the medical procedure, for a preset period of time, or manually controlled. The active pressure control 64 may also be set for a different period of time than the leakage detection monitoring phase 66. For example, the control unit 14 may be configured to be in active pressure control 64 for the first period of time A, between 1 and 2 seconds, and then alternate to the leakage detection monitoring phase 66 for a second period of time B, 10 seconds. The time periods of the active pressure control 64 and the leakage detection monitoring phase 66 may also not be fixed and/or may change over time. In another embodiment, during the medical procedure, the control unit 14 may be configured to be in active pressure control 64 for the first period of time A, one (1) minute and then alternate to the leakage detection monitoring phase 66 for the second period of time B, thirty (30) seconds, or alternatively, the control unit 14 may be configured to be in active pressure control 64 for the first period of time A, thirty (30) seconds and the control unit 14 may be configured to be in active pressure control 64 for the second period of time B, one (1) minute. The control unit 14 may also be configured to remain in active pressure control 64 or alternatively remain in the leakage detection monitoring phase 66 and not alternate. For example, if the leakage detection monitoring phase 66 detects that there may be a leak in the balloon 18 or anywhere else in the cryoablation treatment device 12, the control unit 14 may be configured to remain in the leakage detection monitoring phase 66 to prevent additional gas and/or fluid from being transferred into the balloon 18 while a leak may be present.

Figure 3:
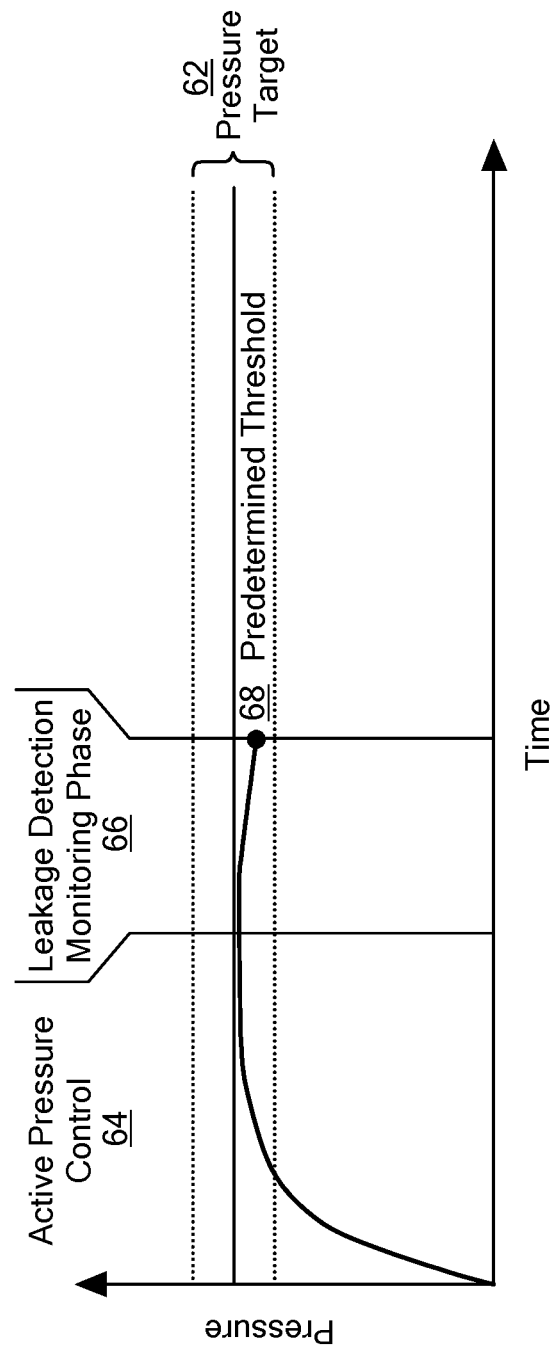
FIG. 3 shows a chart of exemplary data demonstrating the pressure of the expandable element and the processing circuitry alternating between the active pressure control and the leakage detection monitoring phase where the pressure falls below the predetermined threshold and a fault condition is triggered.

Now referring to FIG. 3, active pressure control 64 may be used to initially inflate the balloon 18 with the circulation of fluid and/or gas into the balloon 18 to a pressure within the pressure target 62. Once the balloon 18 is inflated to the pressure within the pressure target 62, the active pressure control 64 may continue to maintain the pressure of the balloon 18 within the pressure target 62. Following the active pressure control 64 where the balloon 18 is inflated to a pressure within the pressure target 62, the control unit 14 may disable the active pressure control 64 for a period of time and activate the leakage detection monitoring phase 66 where the balloon 18 pressure and/or any pressure within the cryoablation treatment device 12 is actively monitored for a period of time. During the leakage detection monitoring phase 66, if the control unit 14 determines that any pressure changes within the balloon 18 and/or anywhere within the cryoablation treatment device 12 exceed a certain predetermined threshold 68, the control unit 14 may signal a fault condition 70. The predetermined threshold 68 may be based upon changes in pressure from a present pressure and/or value or changes in pressure over time. The values set for the predetermined threshold 68 may depend upon the procedure that is being done, the balloon 18 that is being used as well as the design of the control unit 14. The fault condition 70 may be a notification such as an audible alert on the computer 54, a visual alert on the display 56, and/or a tactile alert. The alert may provide information including information about the pressure of the balloon 18, the pressure anywhere within the cryoablation treatment device 12, and any suspected leaks in the balloon 18 or anywhere else in the cryoablation treatment device 12. Additionally and/or alternatively, the fault condition 70 may activate a system response such as shutting down the cryoablation treatment device 12 and/or any portion of the cryoablation treatment device 12 to, for example, avoid the leakage of fluid and/or gas from the medical system 10 into the body of the patient. If the fault condition 70 activates a system response, the system response may be the remove of the refrigerant from the balloon 18 and this may occur with the application of a vacuum to remove refrigerant from the balloon 18 to prevent leakage of the refrigerant into the bloodstream of the patient. The system response may also involve the collection of information to determine the location and/or cause of the leak so that information may be provided by the user of the medical system 10 to help diagnose the issue. This collection of information may occur while any refrigerant is being removed from the medical system 10 and/or after refrigerant is removed from the medical system 10. In one embodiment, as shown in FIG. 3, once the pressure within the balloon 18 and/or anywhere within the cryoablation treatment device 12 falls below the predetermined threshold 68, the fault condition 70 may be triggered. If the fault condition 70 is triggered, the control unit 14 may not return to the active pressure control 64, while notifications and alerts may appear on the medical system 10 and a system response may occur to prevent fluid and/or gas from escaping from the medical system 10 and into the body.

Figure 4:
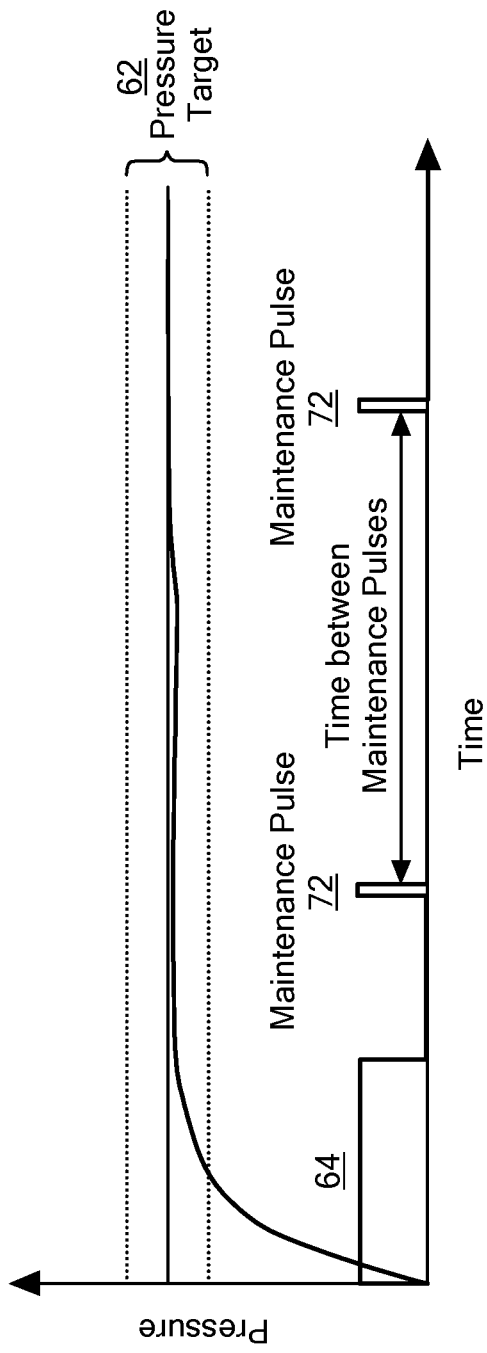
FIG. 4 shows a chart of exemplary data demonstrating the pressure of the expandable element and the processing circuitry providing maintenance pulses at predetermined times where the pressure remained within the predetermined threshold by the periodic maintenance pulses.

Now referring to FIG. 4, in another embodiment, the control unit 14 may be configured to initially trigger the active pressure control 64 to inflate the balloon 18 to a preset pressure within the pressure target 62. The active pressure control 64 may be set to inflate the balloon 18 to a preset pressure over a specified period of time. If the balloon 18 is not inflated to the preset pressure in the specified period of time, the fault condition 70 may be triggered and a notification and/or alarm may go off and/or a system response may be triggered. The failure of the balloon 18 to inflate to the preset pressure in the specified period of time may indicate a leak in the balloon 18 or elsewhere in the medical system 10. During the active pressure control 64, the sensing system 46 may continually monitor the pressure of the balloon 18 or elsewhere within the medical system 10.

Continuing to refer to FIG. 4, if the balloon 18 is inflated to the preset pressure within the pressure target 62 within the specified period of time, the control unit may trigger at least one maintenance pulse 72 to maintain the inflation pressure of the balloon 18. The sensing system 46 may continue to monitor the pressure within the balloon 18 and/or elsewhere in the medical system 10 during the period of time that maintenance pulse(s) 72 are triggered by the control unit 14. The control unit 14 may be configured to monitor the pressure in the balloon 18 and elsewhere in the medical system 10 at all times, including during inflation and deflation of the balloon 18. The maintenance pulse 72 may be a predetermined amount of fluid from the coolant supply reservoir 42 that is delivered through the lumen to the balloon 18 at preset periods of time for a preset duration to maintain the inflation pressure in the balloon 18. The predetermined amount of fluid from the coolant supply reservoir 42 that may be delivered through the lumen to the balloon 18 at preset periods of time may be set to a variety of different parameters based upon, for example, the volume of the balloon 18 and the cryoablation treatment device 12. For example, the maintenance pulse 72 may include a pulse with enough fluid and/or gas to increase the pressure in the balloon 18 by about 0.01 psi per pulse. However, the amount of fluid and/or gas in each maintenance pulse 72 may vary depending on the size of the balloon 18, the control unit 14 design, the length of the catheter as well as other variables. This may be preprogrammed into the medical system 10 or may be configurable based upon the medical system 10 being used. The at least one maintenance pulse 72 may be preset into the control unit 14 based upon the procedure that is being performed and the pressure that is to be maintained with the balloon 18 during the course of the medical procedure, for a preset period of time, or for a manually determined period of time. Accordingly, once the balloon 18 is inflated to a desired pressure, the medical system 10 would only require periodic re-inflation using the maintenance pulses 72 to maintain the desired pressure within the balloon 18. While the medical system 10 may experience some expected loss of pressure in the balloon 18, the expected pressure loss over a particular period of time may be programmed into the control unit 14 so that maintenance pulses 72 may be used at a preset time for a preset duration to maintain the pressure within the balloon 18. Based upon the expected pressure loss over a particular period of time that is equated with the particular balloon 18 pressure, the control unit 14 may be set to initiate maintenance pulses 72 using a predetermined amount of fluid at during preset time intervals. If the balloon 18 is not leaking, the maintenance pulses 72 would be expected to occur at preset time intervals using the predetermined amount of fluid while continuing to maintain the pressure of the balloon 18 within the pressure target 62.

Figure 5:
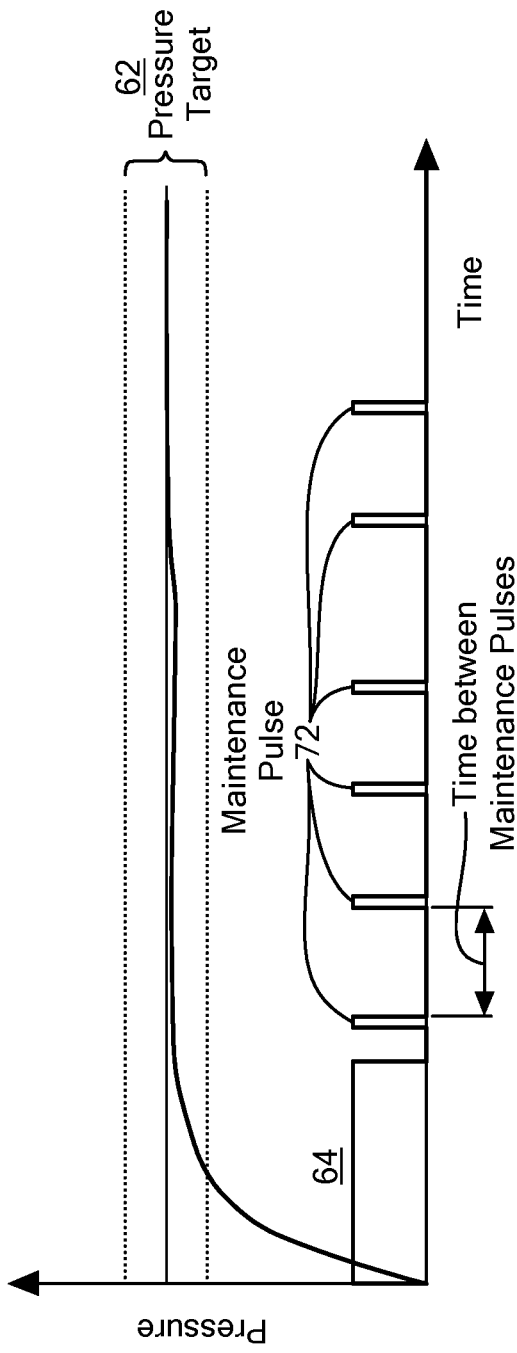
FIG. 5 shows a chart of exemplary data demonstrating the pressure of the expandable element and the processing circuitry providing maintenance pulses at an increased frequency.

Now referring to FIG. 5, if the frequency and/or duration of the maintenance pulses 72 changes from the preset time intervals using the predetermined amount of fluid, the control unit 14 may signal the fault condition 70 to trigger a notification, alarm, and/or system response. In one embodiment, the maintenance pulses 72 may be preset to occur every one (1) minute with a specified amount of fluid and/or gas being released into the balloon 18 during each maintenance pulse 72. The sensing system 46 may be configured to monitor the pressure of the balloon 18 and/or another portion of the medical system 10 before, during and after the maintenance pulses 72. If the pressure in the balloon 18 and/or another portion of the medical system 10 falls below a predetermined pressure threshold between any of the maintenance pulses 72, the control unit 14 may activate maintenance pulses 72 at a different frequency and/or duration with a different amount of fluid being released into the balloon 18 during each maintenance pulse 72. In one example, if the maintenance pulses 72 start occurring with greater frequency than once every one (1) minute, and/or more than the specified amount of fluid is being released into the balloon 18 during the maintenance pulse 72 to maintain the pressure of the balloon 18, a fault condition 70 may be triggered. The change in the amount, duration, and/or frequency of the maintenance pulses 72 may indicate a leak in the balloon 18 and to prevent further leakage of any fluid and/or gas from the medical system 10 into the body of the patient the fault condition may trigger a notification, alarm, and/or a system response. Any preset period of time may be set to trigger each individual maintenance pulse 72 and any amount of fluid and/or gas may be set to be released from the coolant supply reservoir 42 into the balloon 18 during each maintenance pulse 72. The control unit 14 may detect any changes in how often the maintenance pulse 72 is occurring and/or how much fluid and/or gas is being released into the balloon 18 during each maintenance pulse 72. Any changes that are detected by the control unit 14 may trigger the fault condition 70.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for monitoring pressure, the system comprising:
    a medical device, including:
       an expandable element;
       a pressure sensor in communication with the expandable element; and
       a control unit including:
          a fluid source in fluid communication with the expandable element, circulation of the fluid within the expandable element inflates the expandable element; and
          processing circuitry configured to alternate between an active pressure control phase and a leakage monitoring and detection phase,
             wherein the active pressure control phase includes for a first time period, circulating the fluid within the expandable element according to a predetermined target pressure,
             wherein the leakage monitoring and detection phase incudes monitoring a pressure within the expandable element based on signals received from the pressure sensor for a second period of time, wherein
             when a pressure change in the expandable element does not exceed a predetermined threshold during the leakage monitoring and detection phase, the processing circuitry repeats the active pressure control phase,
             when the pressure change in the expandable element exceeds the predetermined threshold during the leakage monitoring and detection phase, the processing circuitry signals a fault condition and discontinues active pressure control phase, and
             the fault condition provides a notification to a user device including at least one selected form the group consisting of an audible alert and a tactile alert.

2. The medical system of claim 1, wherein the processing circuitry alternates between the active pressure control phase and the leakage monitoring and detecting phase for a predetermined period of time.

3. The medical system of claim 2, wherein the predetermined period of time is a duration of a medical procedure.

4. The medical system of claim 1, where the first period of time and the second period of time are the same period of time.

5. The medical system of claim 1, wherein the first period of time is longer than the second period of time.

6. The medical system of claim 1, wherein the first period of time is shorter than the second period of time.

7. The medical system of claim 1, wherein the circulation of the fluid within the expandable element stops when the processing circuitry is monitoring the pressure within the expandable element based on signals received from the pressure sensor.

8. The medical system of claim 1, wherein the expandable element is inflated to a preset pressure with the circulation of the fluid within the expandable element and then the processing circuitry stops the circulation of the fluid within the expandable element for a third period of time.

9. The medical system of claim 1, wherein the fault condition discontinues the fluid circulation in the expandable element.

10. A medical system for monitoring pressure, the system comprising:
    a medical device, including:
       an expandable element; and
       a control unit including:
          a fluid source in fluid communication with the expandable element, circulation of the fluid within the expandable element inflating the expandable element to a preset pressure range, once a pressure of the expandable element is within the preset pressure range, the fluid source provides preset periodic inflation pulses to the expandable element to maintain the preset pressure range; and
          processing circuitry configured to
             periodically monitor at least one selected from the group consisting of a duration and a frequency of the preset periodic inflation pulses to determine any changes to at least one selected from the group consisting of the frequency and the duration of the preset periodic inflation pulses,
             when a pressure in the expandable element falls below a threshold pressure, discontinue providing the preset periodic inflation pulses to the expandable element and signal a fault condition,
             wherein the fault condition provides a notification to a user device including at least one selected form the group consisting of an audible alert and a tactile alert.

11. The medical system of claim 10, wherein the expandable element is a balloon.

12. The medical system of claim 10, wherein the preset pressure range is adjustable.

13. The medical system of claim 10, wherein the frequency and the duration of the preset periodic inflation pluses is adjustable.

14. The medical system of claim 10, wherein a change in at least one selected from the group consisting of the frequency and the duration of the preset periodic inflation pulses signals the fault condition.

15. The medical system of claim 10, wherein the fault condition further provides activation of a system response.

16. The medical system of claim 15, wherein the system response is an evacuation of cryogenic fluid from the medical device and a collection of information to determine at least one selected from the group consisting of a location of a leak in the expandable element and a cause of the leak in the expandable element.

17. The medical system of claim 10, wherein the notification includes at least one selected from the group consisting of information about the pressure of the expandable element, information about the pressure within the medical device, information about a suspected leak in the expandable element, or information about a suspected leak in the medical device.

18. A medical system for monitoring pressure, the system comprising:
   a medical device, including:
      an expandable element;
      a pressure sensor in communication with the expandable element; and
   a control unit configured to operate in a first mode and a second mode:
      the first mode includes circulating a fluid through the expandable element causing the expandable element to inflate for a first period of time and monitoring, with processing circuitry, a pressure within the expandable element based on signals received from the pressure sensor for a second period of time; and
      the second mode includes:
         circulating the fluid within the expandable element in order to inflate the expandable element to a preset pressure range,
         providing, with a fluid source, preset periodic inflation pulses to the expandable element,
         periodically monitoring the preset periodic inflation pulses to the expandable element,
         determining any changes to at least one selected from the group consisting of a frequency and a duration of the preset period inflation pulses, and
         signaling a fault condition and discontinuing providing the preset periodic inflation pulses to the expandable element when the pressure in the expandable element exceeds or falls below the preset pressure range,
      wherein the fault condition provides a notification to a user device including at least one selected form the group consisting of an audible alert and a tactile alert.

* * * * *